United States Patent
Flaction

(10) Patent No.: US 8,157,707 B2
(45) Date of Patent: Apr. 17, 2012

(54) METHOD AND DEVICE ENABLING AN ATHLETE TO DETERMINE AND THEN CONTROL THE RATE OF DISPLACEMENT OF A MASS

(75) Inventor: Patrick Flaction, Chandolin-pres-Saviese (CH)

(73) Assignee: Myotest SA (CH)

( * ) Notice: Subject to any disclaimer, the term of this patent is extended or adjusted under 35 U.S.C. 154(b) by 0 days.

(21) Appl. No.: 13/089,615

(22) Filed: Apr. 19, 2011

(65) Prior Publication Data

US 2011/0207581 A1 Aug. 25, 2011

Related U.S. Application Data

(63) Continuation of application No. PCT/EP2009/063916, filed on Oct. 22, 2009.

(51) Int. Cl.
*A63B 71/00* (2006.01)

(52) U.S. Cl. ............... 482/8; 482/1; 482/3; 482/900

(58) Field of Classification Search ............ 482/1–9, 482/900–902; 434/247; 600/587, 592, 595; 702/141

See application file for complete search history.

(56) References Cited

U.S. PATENT DOCUMENTS

| 5,474,083 | A | 12/1995 | Church et al. | |
|---|---|---|---|---|
| 5,788,655 | A | 8/1998 | Yoshimura et al. | |
| 6,148,280 | A | 11/2000 | Kramer | |
| 7,072,789 | B2 * | 7/2006 | Vock et al. | 702/141 |
| 7,559,877 | B2 * | 7/2009 | Parks et al. | 482/8 |
| 7,603,255 | B2 * | 10/2009 | Case et al. | 702/182 |
| 2006/0191335 | A1 | 8/2006 | Nose et al. | |
| 2007/0219059 | A1 | 9/2007 | Schwartz et al. | |
| 2008/0090703 | A1 | 4/2008 | Rosenberg | |
| 2009/0069722 | A1 | 3/2009 | Flaction et al. | |
| 2010/0211349 | A1 | 8/2010 | Flaction et al. | |

FOREIGN PATENT DOCUMENTS

| DE | 446302 C | 6/1927 |
|---|---|---|
| EP | 1834583 A1 | 9/2007 |
| EP | 2027817 A1 | 2/2009 |
| GB | 2422790 A | 8/2006 |
| JP | 2006122343 A | 5/2006 |
| WO | 03032826 A2 | 4/2003 |
| WO | 2005055815 A2 | 6/2005 |
| WO | 2005074795 A1 | 8/2005 |
| WO | 2007036611 A1 | 4/2007 |
| WO | 2007107491 A1 | 9/2007 |
| WO | 2008030484 A2 | 3/2008 |

OTHER PUBLICATIONS

International Search Report for PCT/EP2009/063691 dated Dec. 1, 2009.

* cited by examiner

*Primary Examiner* — Glenn Richman
(74) *Attorney, Agent, or Firm* — Blank Rome LLP

(57) ABSTRACT

Method enabling an athlete (3) performing a muscular training exercise to determine a setpoint for the rate of displacement of the displaced mass (2), comprising the following steps: 1) determining at least one initial setpoint rate at which said mass has to be displaced; 2) during the athlete's training exercise, measuring a series of acceleration values (a(n)) using a portable accelerometer (30) according to the displacements of said mass; and 3) depending on said series of acceleration values, having said portable accelerometer calculate at least one modified setpoint rate.

12 Claims, 4 Drawing Sheets

METHOD AND DEVICE ENABLING AN ATHLETE TO DETERMINE AND THEN CONTROL THE RATE OF DISPLACEMENT OF A MASS

RELATED APPLICATIONS

The present invention is a continuation of international application PCT/EP2009/063916, filed on Oct. 22, 2009, the contents of which are enclosed by reference. It claims priority of Swiss Patent Application CH2008/01663, the contents of which are enclosed by reference.

In some aspects, the present invention is also related to European Application EP2027817, filed on Aug. 8, 2008, and to European Application EP1834583, filed on Mar. 17, 2006.

TECHNICAL FIELD

The present invention concerns a method and device enabling an athlete to determine and then control the rate of displacement of a mass.

TECHNICAL BACKGROUND

There are many documents describing accelerometers for measuring sport performances. Most of the existing accelerometers are designed for exercises lasting for a long period of time, for example to evaluate the traveled distance or the calorie expenditure during a jogging session or a cycling tour. There are also fairly similar devices for detecting elderly people falling, the time they spend sitting, standing or lying down, etc.

U.S. Pat. No. 5,788,655 (Omron) describes a device designed to be fastened onto the body and provided with an accelerometer and with an LCD. The device continuously measures the wearer's movements to determine his/her level of physical activity and other values depending on the metabolism, such as the user's daily calorie intake. This type of device is useful for measuring more objectively the level of inactivity of patients. It is however not adapted for muscle training and for measuring short efforts, and does not allow for example the maximum power of a muscle group of the athlete to be measured.

WO2005074795 (Nokia) describes a measurement terminal provided with an accelerometer and fastened onto the body of an athlete. The measurement data are assessed to supply a value representative of the intensity of the exerted effort. Again, the aim is to determine the level of activity over a long period, for example a day or a week.

US2006191335 describes a portable accelerometer designed in particular for measuring the muscular force of the legs through walking exercises.

WO03/032826 (Philips) describes a comparable system provided with a three-axis accelerometer for determining the level of physical activity of a patient. The proposed device displays values such as the daily metabolic rate, the daily energy output or the energy output induced by exercise. This device is thus useful for measuring accelerations over a period of several hours or even of several days.

None of these devices allows basic physiological muscle parameters such as strength, speed or power of a muscle group to be obtained. They are essentially suited for endurance sports, for example for jogging, and are not or only poorly adapted for the specific training of the force, power or speed of contraction of a muscle or muscle group. Without knowing the displaced mass, many devices do not make it possible to deduce the athlete's force or power. Even if this mass is known, many devices aim first and foremost to calculate the distance travelled, the average speed or the energy output, but do not allow the muscle power of a muscle group of the athlete to be determined directly, i.e. the speed at which this muscle group can displace a given mass.

U.S. Pat. No. 5,474,083 describes a system designed to monitor the load-lifting movements of a patient. The system uses electrodes for measuring the activity of the patient's muscles during the movement, as well as a load movement detector. An alarm is triggered in case of inappropriate movement. This system is useful for preventing accidents caused by incorrect load lifting or for having people practise lifting loads without injury. It is however not suited for measuring the athlete's muscular performance. Furthermore, the use of electrodes makes it inconvenient to use.

U.S. Pat. No. 6,148,280 (Virtual Technologies) describes a device provided with accelerometers and gyroscopes placed on the entire body of an athlete. The data supplied by several sensors are transmitted to a PC that allows the trajectory and other features of the movement to be analyzed. This system is complex, since it makes use of several sensors, including expensive and relatively fragile gonometers. The connection of the sensors to one another and with the external computer increases the cost of the device and makes it difficult to install. It is adapted for training precise movements, for example a golf swing, but does not allow the muscle power developed by the athlete during this movement to be determined directly.

DE446302 describes an accelerometer used in combat sports for measuring the acceleration of the strike surface. The apparatus is not portable and is suited only to combat sports such as boxing, karate, etc. An external computer must be used to assess and display the results of the measurement. It is not programmable and can be used only for a single type of exercise.

WO2007036611 (Oulun Seudun Ammattikorkeakoulu) describes a wristlet provided with an accelerometer for measuring muscular force during a load-lifting movement.

Application WO07107491 describes a portable accelerometer enabling the muscle power of an athlete or of a patient to be assessed using short tests. These tests make it possible to determine the athlete's maximum power and to select the optimum load with which an athlete must exercise to maximize the power expended during the exercise.

However, this device supplies no indication to the athlete as to the rate at which this load is to be displaced in order to achieve the desired results. Furthermore, the recommendations do not depend on qualitative objectives of the athlete nor on the performances the athlete wishes to improve. For example, this device does not distinguish between an athlete wishing to improve speed and another athlete wishing to improve power. Finally, this device is designed for short tests only, using a series of exercises imposed by the device (for example 5 jumps, 5 lifts, etc.); an error is generated if the athlete executes different movements or a different number of movements from what is prescribed by the test. This devices is thus not adapted for measuring physiological parameters during training, for example when the number of movements varies.

Other accelerometers used for measuring muscular parameters are also described in GB2422790 and in WO20005055815.

BRIEF SUMMARY OF THE INVENTION

There is thus a need in the state of the art for a method and a device for improving the efficiency and the quality of the training plans of any athlete in the field of sports.

There is also a need for a new accelerometer designed for sporting activities and that enables the muscle power of a given muscle or group of muscles to be measured.

There is also a need for an accelerometer and for a method enabling an athlete to determine training setpoints, i.e. values for the mass to be displaced, rate of displacement and/or number of displacements or series of displacements, in order to improve the muscle power of a specific muscle or muscle group. Muscle power is understood in the present application to be the ability to displace a given mass at a given speed for a given number of times.

There is also a need for an accelerometer and for a method allowing the compliance with these setpoints during training to be controlled and enabling these setpoints to be adapted to the progress and measurements during training.

According to the invention, these aims are achieved notably by means of a method for the muscle training of an athlete by repeated displacements of a mass, comprising the following steps:
1) determining at least one initial setpoint rate at which said mass has to be displaced;
2) during the athlete's training exercise, measuring a series of acceleration values (a(n)) using a portable accelerometer (30) according to the displacements of said mass; and
3) depending on said series of acceleration values, having said portable accelerometer calculate at least one modified setpoint rate.

According to one aspect, the method enables the athlete to determine the optimum mass to be lifted for each type of exercise, depending on the athlete's objectives, as well as the speed or rate at which this mass must be lifted. During training, the inventive device makes it possible to check whether the mass is indeed lifted at the correct rate and to then adapt the mass and rate setpoints for future training sessions according to the measured acceleration values.

BRIEF DESCRIPTION OF THE FIGURES

Examples of embodiments of the invention are indicated in the description illustrated by the attached figures in which.

EXAMPLE(S) OF EMBODIMENTS OF THE INVENTION

Figure 1:
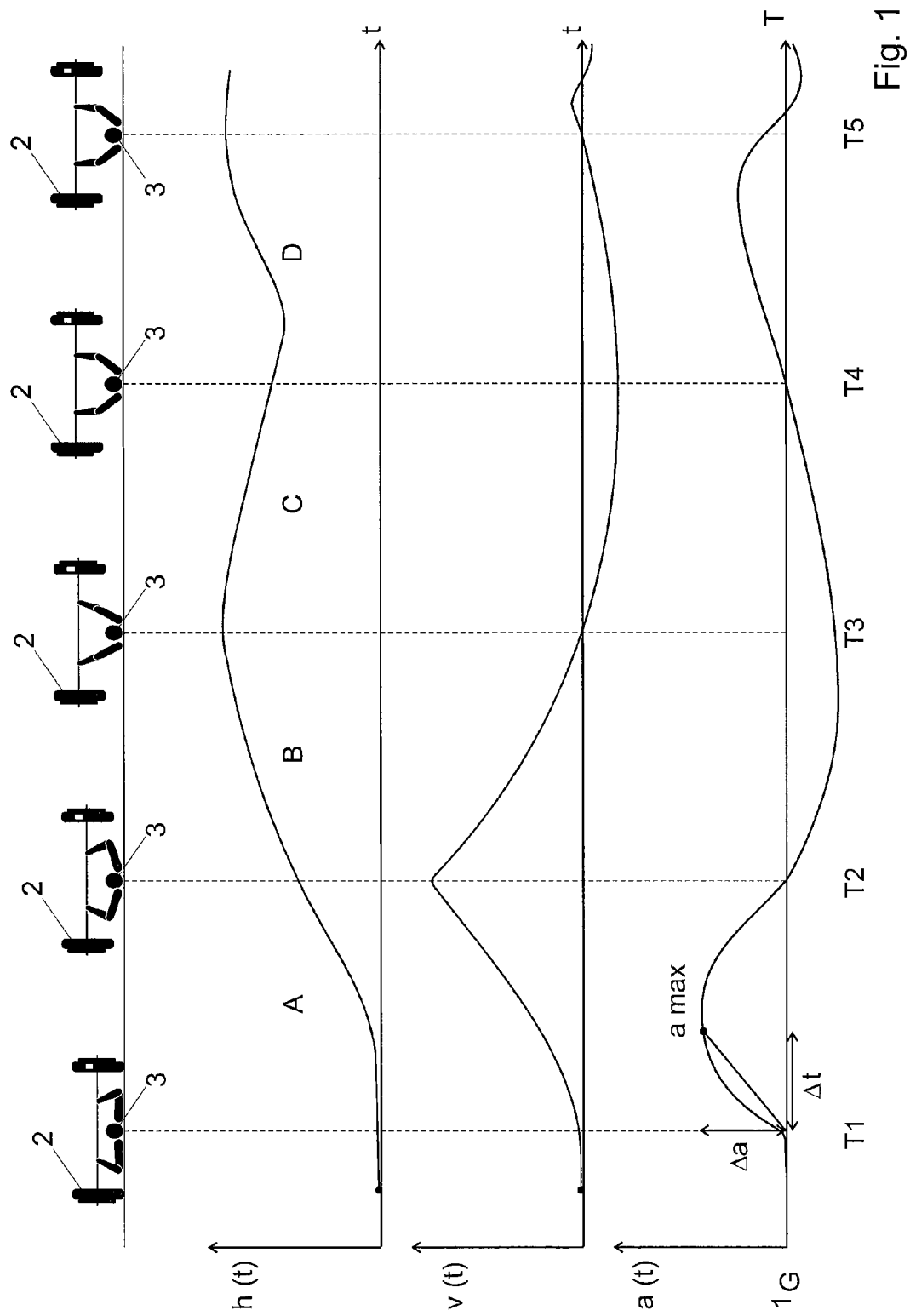
FIG. 1 illustrates diagrammatically different phases of the movements of an athlete during a load-lifting movement of the type "bench-press".

FIG. 1 illustrates the evolution of different kinematic parameters during a load-lifting movement of the type "bench-press". This movement, often used in muscle training, consists in lifting a load 2 with both arms, from a position lying on the back. The load is lifted as high as possible by combining an adduction of the shoulder and an extension of the elbow. The upper line of FIG. 1 illustrates five phases of the movement. The exercise starts at T1, in the initial position represented on the first image on the left of FIG. 1. The load is at its lowest point (h(t)=0), the elbows of the athlete 3 are bent.

During phase A, between the instants T1 and T2, the athlete 3 lifts the load whose speed v(t) and height h(t) increase constantly, as indicated on the corresponding graphs. The pushing force (proportional to the acceleration a(t)) exerted during this phase is at its maximum and the arms extend.

During phase B, between the instants T2 and T3, the pushing continues but the lift speed v(t) diminishes; the acceleration a(t) then becomes less than 1G (earth gravitation), as seen on the lower graph of FIG. 1. The load height is at its maximum at the point T3.

The athlete 3 then relaxes his/her effort during phase C between the key instants T3 and T4. The load then moves back down slightly, so that its speed becomes negative. This stage is then followed by a stabilizing phase D, between the instants T4 and T5, during which the athlete maintains his/her arms extended but tends to lower his/her shoulders. The acceleration the load 2 is subjected to during this phase tends progressively towards 1G.

Figure 5:
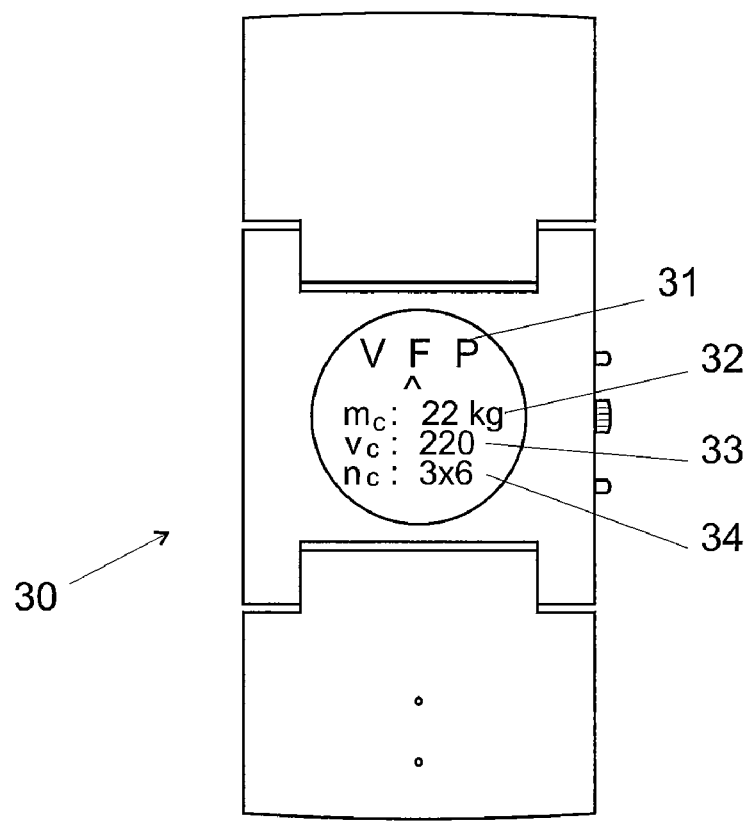
FIG. 5 is a top view of an example of a portable accelerometer.

The acceleration to which the lifted load is subjected can be measured by an accelerometer connected to the mass displaced, for example a three-axis accelerometer connected to the mass 2 by a hook and loop fastener, for example an accelerometer mounted in a case similar to that described in international application WO07EP052413. In a preferred embodiment, the acceleration is measured by means of an accelerometer 30 mounted in a wristwatch worn by the user, such as illustrated in FIG. 5; the athlete's wristwatch follows approximately the displacements of the mass lifted by the athlete and is subjected more or less to the same accelerations.

Apart from the bench press, the device and method of the invention can also be used with other types of exercises for training the muscle power of other muscle groups, through repetition of quick displacements of a known mass. For example, the invention applies to other load lifting exercises, load displacements against a force, jumps etc. More generally, the invention applies to different types of muscle power training by a series of brief displacements of a known mass, each time that the acceleration to which this mass is subjected can be measured with a portable accelerometer. The method can imply a selection by the user of the type of exercise performed, so as to configure the accelerometer.

Figure 6:
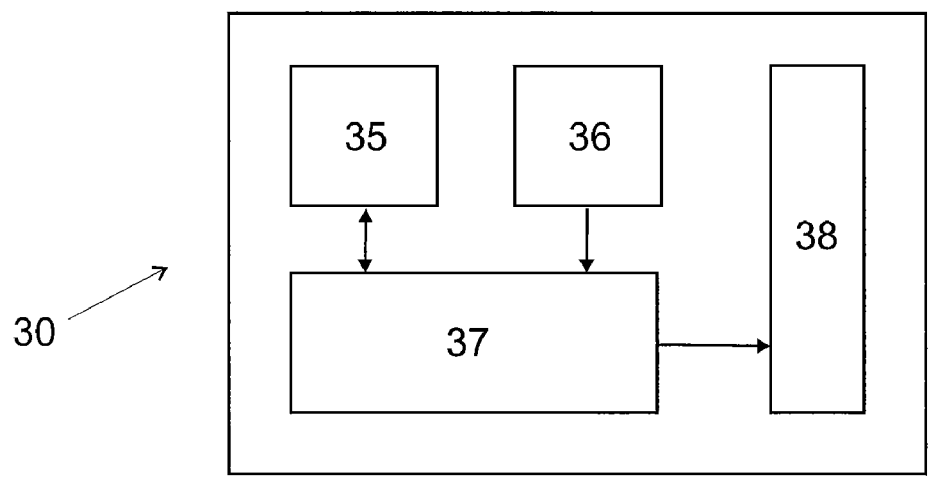
FIG. 6 is a bloc diagram of an example of a portable accelerometer.

An example of accelerometer 30 is illustrated with the aid of the block diagram of FIG. 6. This accelerometer can be integrated in the wristwatch of FIG. 5 or in another portable casing. It preferably comprises an acceleration sensor 36, preferably a three-axis sensor allowing the acceleration to be determined by projection according to the displacement trajectory, for example the acceleration along the vertical direction. A three-axis accelerometer is particularly advantageous when the sensor is integrated in a bracelet that can find itself in different positions depending on the movement. The sensor 36 can also integrate a gyroscope, for example a three-axis gyroscope, although this increases the cost of the device and is not required for the present invention.

The successive acceleration values supplied by the accelerometer 36 are transmitted to a microcontroller 37 executing a program stored in a memory 35. The acceleration data and/or values derived from these data can also be stored in this memory 35. The microcontroller 37 can also reproduce visual and/or audio signals on reproduction means 38, for example an LCD screen and/or speakers. It is also possible to transmit these data to a remote processing system, for example over a wired interface of the type USB for example, or a wireless interface of the type Bluetooth or Zigbee for example. The accelerometer 30 is preferably electrically autonomous and portable, for example on the wrist.

The microcontroller 37 thus makes it possible to acquire a series of acceleration values during training, then to calculate during training and/or at the end of this training other values derived from this acceleration. The values calculated by the microcontroller 37 from the series of acceleration data can include for example the rate of displacement of the mass, its height, the athlete's energy output, his/her power etc.

With reference again to FIG. 1, the speed calculated and/or stored can correspond for example to the maximum speed during displacement, to the average speed, to the instantaneous speed during certain key instants etc. In one embodiment, the accelerometer determines only the time between two key instants, for example the flight time during a jump or the duration of the phases A and B of FIG. 1 during a bench press. In this case, the speed setpoint can correspond to a duration, with the distance of displacement being implicit or assumed to be constant.

Before beginning a training session for a muscle group, an athlete must select the mass to be displaced as well as the rate at which it is to be displaced. S/he can also select the number of displacements or the series of displacements in order to achieve his/her objectives, or the duration of training, or even decide to interrupt manually the training in the course of the exercise. According to the invention, these setpoints, which are traditionally set empirically or by a trainer, are selected by the claimed portable accelerometer, which can also help the athlete to follow them. Preferably, these setpoints are selected on the basis of measurements performed during an initial test with the accelerometer and by indicating the type of training chosen.

Figure 2:
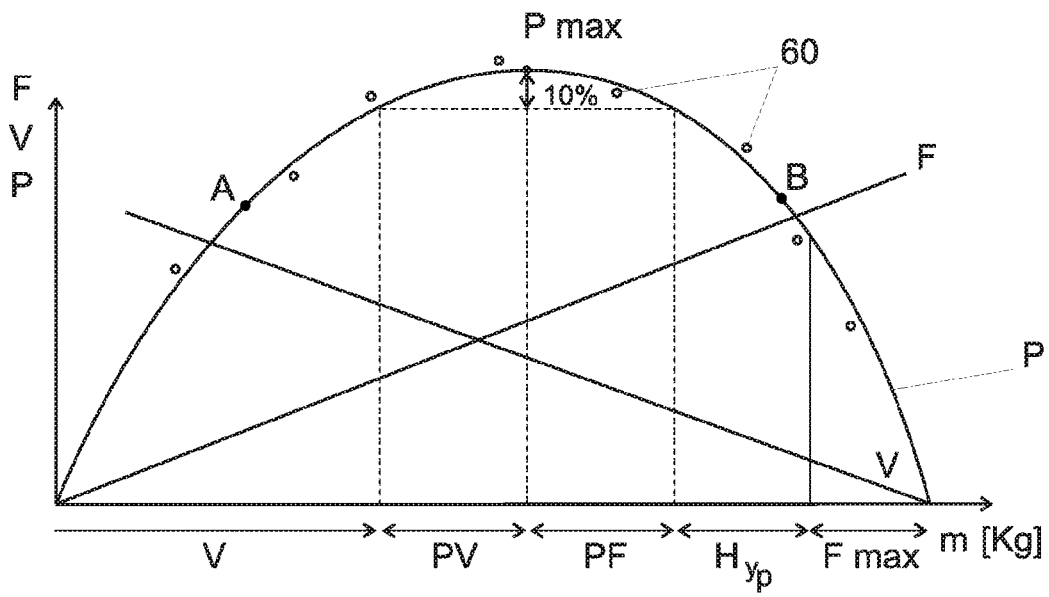
FIG. 2 illustrates diagrammatically a possible evolution of the force F, of the speed V and of the power P expended by an athlete lifting different loads of variable mass m.

FIG. 2 illustrates diagrammatically a possible evolution of the force F, of the speed V and of the power P expended by an athlete 3 lifting different charges 2 of variable mass m. The gravitational force F=m×g exerted on the load used increases in a linear fashion with the load's mass. On the other hand, the lifting speed V diminishes when the lifted mass increases; the athlete lifts light masses more rapidly.

The power P during the effort thus goes through an optimum for a given value of the lifted mass m, as indicated in the above-mentioned application WO07107491. The relation P=f(m) specific to an athlete can be obtained for example by interpolation and/or extrapolation calculations from a series of measurements 60 (profile) performed by making the athlete lifting variable loads. In practice, 4 to 8 measurements with different loads make it possible to determine the muscular profile of an athlete with sufficient accuracy.

This personalized power curve makes it possible to determine the load with which the athlete must train to obtain different types of results. A maximum power gain can be achieved by training with the mass value corresponding to Pmax. An athlete wishing to improve his/her speed will preferably train in the training range V, i.e. with a light mass lifted with a power lower than the maximum power. The range PV (power and speed) corresponds to masses that are lighter than the optimum mass and requiring a power close to the maximum power. PF (power force) also requires considerable power close to the maximum power but with heavier masses. A muscular hypertrophy for bodybuilding enthusiasts will be achieved by lifting heavy masses slowly (range of values Hyp). The range $F_{max}$ beyond Hyp corresponds to extremely heavy masses lifted very slowly, for pure force training.

It can be seen that knowing the muscular profile of an athlete makes it possible to determine the mass to be lifted and the rate of displacement of this mass in order to achieve the qualitative objectives of the athlete. By knowing these qualitative objectives (i.e. the type of training s/he wishes to perform in order to improve his/her speed, power or force etc.), this profile enable personalized training setpoints to be determined, i.e. the mass and speed values that allow training in the selected zone (V, PV, PF, Hyp) to be performed.

In order to determine his/her muscular profile and thus select setpoints for the mass and rate of displacement, an athlete can perform a test, for example a series of lifts or jumps, preferably with variable loads and with the measurement, using an accelerometer, of the mass's speed during this exercise. Such a test must be carried out before training and then repeated regularly in order to measure the progress achieved and adapt the training plan accordingly. Many users however consider the time and effort devoted to the test (which are added to the time and effort of the training itself) to be taxing. Furthermore, even a weekly muscular profile test does not take into account variations in the physical form of each person throughout the week.

In order to avoid these disadvantages, in an advantageous embodiment of the invention, setpoint values are determined or adapted according to the measurement of acceleration values performed throughout the training, instead of determining them using an additional test session. These setpoints can advantageously be determined with an accelerometer 30 such as the one illustrated in FIG. 5 and integrated in a wristwatch worn by the athlete.

Figure 4:
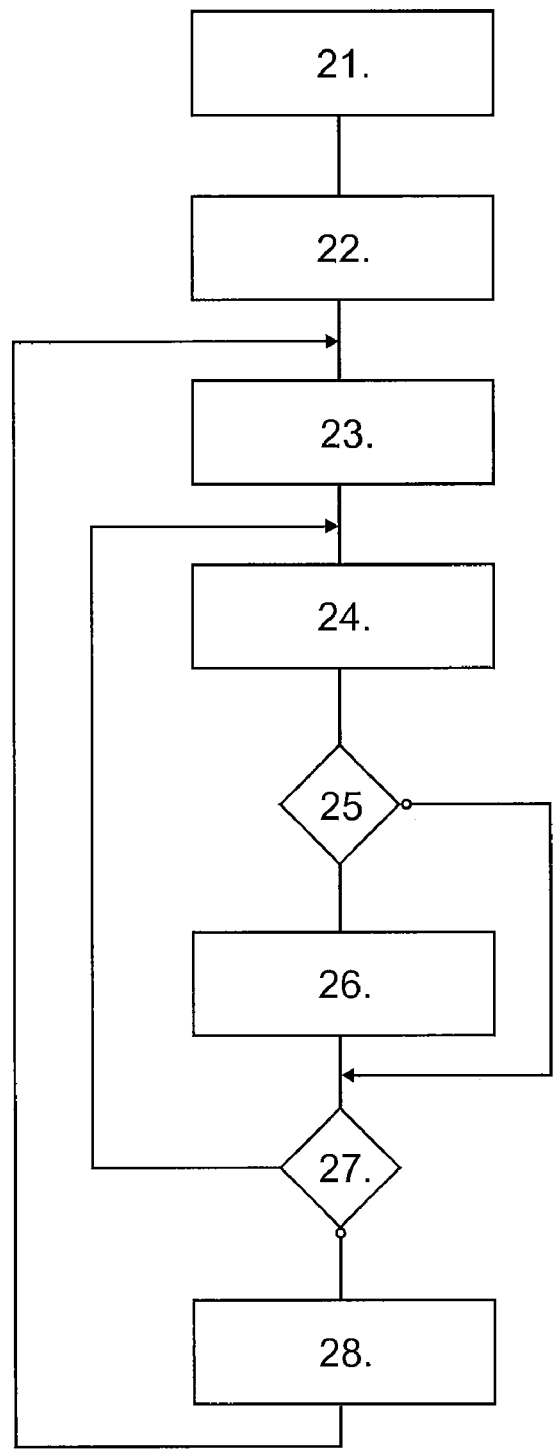
FIG. 4 is a flow diagram illustrating different steps of an example of the method.

FIG. 4 illustrates an example of a method for determining and controlling muscle training setpoints, i.e. values for the mass $m_{setpoint}$ to be lifted, for the recommended rate of displacement of this mass $v_{setpoint}$ and/or for the number $n_{setpoint}$ of displacements or series of displacements to be performed during training. For certain exercises, for example jumps, the mass m can be fixed and correspond for example to that of the athlete.

During the steps 21-23, the device 30 first determines initial setpoint values for the displacement rate, for the mass that is to be displaced at this speed and finally for the number of displacements to be performed. In one embodiment, these initial values are pre-selected in the device, and are for example identical for all the users, or depend only on general parameters entered by the user such as age, weight, gender, level of fitness (beginner, advanced, etc.). In another embodiment, the user can enter into the accelerometer initial setpoint values that have been for example determined with another accelerometer or suggested by a coach.

In a preferred embodiment, these initial setpoints are determined by the accelerometer 30 by making the athlete perform a muscular profile test 21 comprising a limited number of variable mass displacements. The displacement rate of these different masses is measured by the accelerometer 30; the microcontroller 37 then determines by interpolation and extrapolation a complete muscular profile of the athlete and/or determines according to these measured acceleration values initial setpoint values.

In a step 22, the athlete entered into the accelerometer 30 its qualitative objectives, for example if s/he wishes to train speed, power, force etc. This selection can for example be performed by selecting, by means of control elements of the watch, a value in a list 31 of predefined objectives. The accelerometer 30 can also suggest a choice, for example a choice depending on the measurement results during the test 21 or in the course of the previous training sessions. In one embodiment, the selection is entered by indicating the sport the athlete wishes to practise.

The accelerometer 30 then computes during step 23 a setpoint value $v_{setpoint}$ for the speed and possibly a setpoint value $m_{setpoint}$ for the mass as well as a setpoint $n_{setpoint}$ for the number of displacements that are to be performed in order to achieve the set qualitative objectives, taking into account the muscular profile determined during the step 21 and/or previous training sessions.

In one embodiment, these setpoint values are displayed or reproduced by the accelerometer, for example by means of an LCD (fields 32-34).

Once these initial setpoint values have been determined, the athlete then trains during step 24 by displacing the determined setpoint mass $m_{setpoint}$ at the prescribed setpoint rate $v_{setpoint}$ during the prescribed duration for the prescribed number of times or until the end of the training session. Typically, the number of displacements during a training session is much greater than during the initial test 21. The initial profile test comprises for example 4 to 8 movements, possibly with different loads, whilst a training session includes for example 3 series of twelve displacements with a fixed mass or with a mass that changes only between the different series.

During this training 24, the accelerometer 30 measures the acceleration to which the displaced load 2 is subjected and determines in real time the displacement rate as well as possibly other values depending on this acceleration. The accelerometer 30 can also control the number of displacements and of series of displacements performed, as will be seen further below.

Figure 3:
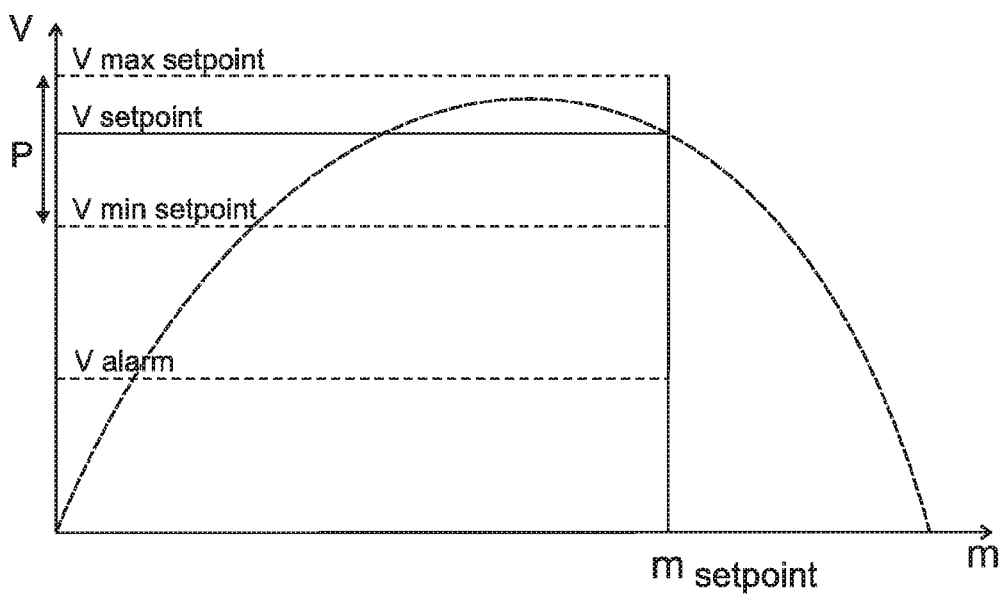
FIG. 3 illustrates diagrammatically the speed range around the fixed setpoint rate.

When the athlete displaces the mass 2 too fast or too slowly, i.e. outside a range p of setpoint rate (FIG. 3), the accelerometer detects this deviation (step 25) and then generates during step 26 an alarm inviting the athlete to correct this speed. In a preferred embodiment, different alarm signals are generated in the form of acoustic signals. For example, a series of quick and high-pitched beep-beep-beeps can be generated in case of a displacement that is too quick and lower and slower BUUP---BUUP in case of a displacement below $V_{min\_setpoint}$. However, the exercise and the measuring of the acceleration are not interrupted when the setpoint rate range p is exceeded only slightly. The accelerometer 30 thus enables the athlete to make sure that s/he is indeed training at the setpoint rate recommended to achieve the qualitative objectives.

In case of a significant speed undershoot or overshoot, for example if the athlete does not succeed in displacing the setpoint mass above the very low speed $V_{alarm}$, a different alarm signal, for example a strident alarm signal, can be generated to invite the athlete to interrupt training immediately. The accelerometer 30 thus serves as security device for preventing injury if the athlete is practically no longer able to lift the prescribed masses.

Other signals can be generated throughout training by the accelerometer, including visual signals displaced on the device and/or voice messages generated for example by a voice synthesizer.

During step 27, the accelerometer checks if the training session is finished. The method returns to step 24 as long as training has not finished. If the test is finished, for example when the athlete has performed the number of displacements $n_{setpoint}$ provided according to the qualitative objectives or in the other cases where the test is interrupted, the accelerometer preferably generates another acoustic signal. It thus also serves as displacement counter and allows for example the athlete to know immediately during training that the prescribed number of displacements $n_{setpoint}$ has been performed. It is also possible to control the athlete's rhythm during training and to generate a signal at the beginning of each displacement or in case of a pause exceeding a predetermined duration.

In a preferred embodiment, the accelerometer continues to acquire measurements even if the athlete produces his/her effort beyond the prescribed number of displacements $n_{setpoint}$. The acquisition in this case ends when the user selects a key to this effect or if the accelerometer detects a long period without any motion or a displacement that does not correspond to the expected exercise (for example if the athlete gets up again).

The accelerometer then goes on to step 28 during which the results of measurements made during the test, or values calculated from those values, are preferably displayed. The accelerometer can for example display the number of displacements performed, the energy output, the maximum power applied etc. The accelerometer then returns to step 23 during which new setpoint values for the speed and possibly for the mass and/or number of displacements are calculated according to the series of acceleration values during training. These new setpoint values are preferably displaced or otherwise reproduced to the user and will be used for further training.

The accelerometer thus makes it possible to follow constantly the progress achieved by the athlete and to adapt at the end of each training session (or even during this training) the setpoint values according to the measured acceleration measurements and to the speed computed from this acceleration. For example, if the microcontroller 37 observes that the user experiences difficulties in displacing the setpoint mass at the prescribed setpoint rate, it can reduce the setpoint rate and/or the setpoint mass and/or the number of displacements required. Conversely, if the user tends to displace this mass more quickly than the optimum setpoint speed, the accelerometer can recommend training with heavier loads, quicker displacements and/or increased series.

Setpoint values can be adapted even if the user constantly displaces the setpoint mass within the speed range between $v_{max\_setpoint}$ and $v_{min\_setpoint}$. For example, a displacement rate that is constantly above the setpoint speed, although always within the range p, does not generate any alarm during training but can nevertheless cause a modification of the setpoint values for future training.

The adaptation of the setpoint values can also depend on the evolution of the athlete's ability to follow the setpoints during a training session. For example, the microprocessor 37 can detect situations in which the athlete manages without difficulties to displace the required masses at the setpoint rate at the beginning of the training session but quickly tires and proves incapable of applying this rate during the last displacements. It is also possible to react to the length of the breaks taken by the athlete between two successive displacements of the mass 2, independently of the rate at which this mass is displaced.

Even if the athlete trains with a setpoint mass $m_{setpoint}$, the acceleration values measured during training can influence the speed setpoint and/or the number of displacements applied to subsequent training with another mass. It is indeed possible that an athlete who has significantly improved his/her performances in the training zone PV (power-speed) of FIG. 2 will also observe progress if training in the zone PF (power-force) or in the zone F (force). Speed measurements carried out with a given mass thus have an influence on the athlete's entire muscular profile, even for other mass values.

Setpoint values can also depend on the progress achieved by the athlete in the course of several consecutive sessions. For example, the microprocessor can take into account quick progress achieved by an athlete at the beginning of a training plan, then detect a plateauing of the performances or a fatigue of the athlete during subsequent training sessions. In this case, the accelerometer 30 can for example propose different training exercises or rest/recovering sessions in order to take this stagnation into account. For this purpose, the accelerometer 30 can store setpoint values successively proposed during different training sessions, in connection with a training date and hour (training frequency), as well as the results (for example the average, median, minimum and/or maximum speed) achieved during each training with these setpoint values.

The accelerometer 30 can also propose, and control compliance with, training plans comprising several sessions separated by several hours or several days. For example, depending on the athlete's qualitative and/or qualitative objectives, the accelerometer can propose several training sessions per week, with masses, speeds and/or numbers of displacements different for each session. This plan is adapted when the athlete does not follow it, for example if a session is missed, if it is not performed on the set days, or if the set masses cannot be displaced at the set speeds, or conversely if the athlete's progress are quicker than expected. In this case, the accelerometer can suggest deleting, adding or moving training sessions provided in a training plan.

The controlling of the displacement rate of the mass throughout the training makes it possible to provide new training plans difficult to implement without this control operation. For example, training plans comprising displacements of variable (for example increasing) masses at constant speed can be proposed and controlled with this accelerometer.

The accelerometer of the invention thus makes it possible to plan training sessions by setting the speed as training setpoint instead of the power, as is the case for conventional training. The points A and B on the graph of FIG. 2 correspond to displacements at equal power—the displacement rate as well as the mass however vary significantly between these two points, as well as the effects of this training on the athlete. In this case, the choice between training with the setpoint values corresponding to the point A or B depends only on the athlete's qualitative objectives.

As indicated above, the selection of the setpoint values depends furthermore on the type of exercise performed by the athlete. The accelerometer preferably allows the user to select a type of exercise from a list of available exercises or to define his/her own exercise. The recommendations and computation of setpoint values then depend on the type of exercise selected or entered.

The invention claimed is:

1. Method enabling an athlete performing a muscular training exercise to determine a setpoint for the rate of displacement of the displaced mass, comprising the following steps:
   1) determining at least one initial setpoint rate at which said mass has to be displaced;
   2) entering, by the athlete, into the portable accelerometer of a qualitative objective for training;
   3) during the athlete's training exercise, measuring a series of acceleration values using said portable accelerometer according to the displacements of said mass; and
   4) depending on said series of acceleration values, having said portable accelerometer calculate at least one modified setpoint rate, with at least one setpoint value calculated by said accelerometer being dependent on said qualitative objective.

2. The method of claim 1, wherein said accelerometer makes it possible to determine a setpoint for the mass to be displaced according to the acceleration measurements performed during training.

3. The method of claim 1, wherein said accelerometer makes it possible to determine a setpoint for the number of displacements and/or series of displacements of the mass to be displaced during training, according to the acceleration measurements performed during training.

4. The method of claim 1, wherein said accelerometer makes it possible to determine a training plan defining setpoints relative to several distinct training sessions, according to the acceleration measurements performed during training.

5. The method of claim 1, wherein the portable accelerometer reproduces to the athlete a signal during training to inform him/her that the displacement rate of said mass lies outside a speed range around the setpoint rate.

6. The method of claim 5, wherein said accelerometer generates a first acoustic signal when the displacement rate of said mass is lower than the minimum of said speed range,
   and a second acoustic signal when the displacement rate of said mass is greater than the maximum of said speed range.

7. The method of claim 5, wherein the measuring of acceleration values is continued even if the displacement rate of said mass lies outside said speed range.

8. The method of claim 1, wherein said qualitative objective is entered by selecting an objective from a list of objectives.

9. The method of claim 1, comprising a step of displaying a list having one or several of the following elements:
   a) speed
   b) power-speed
   c) power-force
   d) hypertrophy
   e) force
   and a step of entering at least one qualitative objective selected in this list.

10. The method of claim 8, wherein selecting said objective modifies both the speed setpoint and a setpoint for the mass to be displaced.

11. The method of claim 10, wherein said modified setpoint rate is computed at the end of said training session and stored in said portable accelerometer.

12. The method of claim 1, wherein said portable accelerometer is integrated in a wristwatch.

* * * * *